United States Patent
Chikamatsu et al.

(10) Patent No.: US 8,134,701 B2
(45) Date of Patent: *Mar. 13, 2012

(54) DEFECT INSPECTING METHOD AND APPARATUS

(75) Inventors: Shuichi Chikamatsu, Konosu (JP);
Minori Noguchi, Joso (JP); Kenji Aiko, Ninomiya (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/774,379

(22) Filed: May 5, 2010

(65) Prior Publication Data
US 2010/0214561 A1    Aug. 26, 2010

Related U.S. Application Data

(60) Continuation of application No. 12/428,065, filed on Apr. 22, 2009, now Pat. No. 7,733,475, which is a division of application No. 11/717,651, filed on Mar. 14, 2007, now Pat. No. 7,535,561.

(30) Foreign Application Priority Data

Mar. 14, 2006 (JP) .................................. 2006-068479

(51) Int. Cl.
*G01N 21/00* (2006.01)
(52) U.S. Cl. ............... 356/237.2; 356/237.3; 356/237.4; 356/237.5
(58) Field of Classification Search .................. None
See application file for complete search history.

(56) References Cited

U.S. PATENT DOCUMENTS

| 5,473,426 | A | 12/1995 | Hayano et al. |
|---|---|---|---|
| 5,694,214 | A | 12/1997 | Watanabe et al. |
| 5,844,850 | A * | 12/1998 | Tsutsui et al. ................ 365/200 |
| 6,014,455 | A | 1/2000 | Sumiyoshi et al. |
| 6,324,298 | B1 * | 11/2001 | O'Dell et al. ................. 382/149 |
| 6,721,047 | B2 | 4/2004 | Shimoda et al. |

(Continued)

FOREIGN PATENT DOCUMENTS

JP    62-89336    4/1987

(Continued)

OTHER PUBLICATIONS

Office Action issued in Japan on Oct. 22, 2010 with partial English translation.

(Continued)

*Primary Examiner* — Tarifur Chowdhury
*Assistant Examiner* — Gordon Stock, Jr.
(74) *Attorney, Agent, or Firm* — McDermott Will & Emery LLP

(57) ABSTRACT

A defect inspecting apparatus of the invention solves a problem that in a defect inspecting apparatus, because of improving detection sensitivity of a microscopic defect by reducing a detection pixel size, a focal depth becomes shallow, a height of imaging is varied due to environmental change and the detection sensitivity of a defect becomes unstable. This apparatus comprises an XY stage, which carries a substrate to be inspected and scans in a predetermined direction, and a mechanism having a system of irradiating a defect on the inspected substrate at a slant and detecting the defect by a detection optical system disposed on the upper side, which corrects a height of imaging in real time for change in temperature and barometric pressure in order to keep the imaging in a best condition.

5 Claims, 7 Drawing Sheets

U.S. PATENT DOCUMENTS

| | | |
|---|---|---|
| 7,037,735 B2 | 5/2006 | Noguchi et al. |
| 7,068,364 B2 | 6/2006 | Sugihara et al. |
| 7,535,561 B2 * | 5/2009 | Chikamatsu et al. ...... 356/237.2 |
| 7,733,475 B2 * | 6/2010 | Chikamatsu et al. ...... 356/237.2 |
| 2003/0044058 A1 | 3/2003 | Tada |
| 2004/0070753 A1 * | 4/2004 | Sugihara et al. ........... 356/237.5 |
| 2005/0146715 A1 * | 7/2005 | Lin et al. ................... 356/237.4 |
| 2007/0057184 A1 | 3/2007 | Uto et al. |
| 2008/0002195 A1 | 1/2008 | Otani et al. |
| 2009/0262339 A1 | 10/2009 | Suga et al. |

FOREIGN PATENT DOCUMENTS

| | | |
|---|---|---|
| JP | 63-135848 | 6/1988 |
| JP | 1-117024 | 5/1989 |
| JP | 1-250847 | 10/1989 |
| JP | 04-350613 | 12/1992 |
| JP | 5-218163 | 8/1993 |
| JP | 6-258239 | 9/1994 |
| JP | 6-324003 | 11/1994 |
| JP | 8-210989 | 8/1996 |
| JP | 8-271437 | 10/1996 |
| JP | 2000-105203 | 4/2000 |
| JP | 2001-60607 | 3/2001 |
| JP | 2001-512237 | 8/2001 |
| JP | 2001-264264 | 9/2001 |
| JP | 2002-90311 | 3/2002 |
| JP | 2004-61289 | 2/2004 |
| JP | 2004-177284 | 6/2004 |
| JP | 3566589 | 6/2004 |
| WO | WO 99/06823 | 2/1999 |

OTHER PUBLICATIONS

Japanese Office Action, w/ English translation thereof, issued in Japanese Patent Application No. 2006-068479, dated Sep. 6, 2011.

* cited by examiner

DEFECT INSPECTING METHOD AND APPARATUS

RELATED APPLICATIONS

This application is a continuation of U.S. patent application Ser. No. 12/428,065, filed on Apr. 22, 2009, now U.S. Pat. No. 7,733,475, which is a divisional of U.S. patent application Ser. No. 11/717,651, filed on Mar. 14, 2007, now U.S. Pat. No. 7,535,561, claiming priority of Japanese Patent Application No. 2006-068479, filed Mar. 14, 2006, the entire contents of each of which are hereby incorporated by reference.

BACKGROUND OF THE INVENTION

The present invention relates to an inspection method and inspecting apparatus, particularly to a technology suitable for inspecting the generation state of a defect such as a particle etc. in a manufacturing process by inspecting a defect such as a particle etc. produced in the manufacturing process for forming a pattern on a substrate to manufacture an object, such as a semiconductor manufacturing process, a liquid display element manufacturing process, and a printed circuit board manufacturing process, analyzing and taking measures.

In a semiconductor manufacturing process, a particle on a semiconductor substrate (wafer) may cause a failure such as an insulation failure or shot-circuit. Further, as semiconductor elements become miniaturized, if a microscopic particle is present, the microscopic particle may cause an insulation failure of a capacitor or breakdown of a gate oxide film. Such a particle comes to be mixed in, with taking various forms such as a particle produced from a moving part of a carrier device or a human body, a matter created by reaction of a process gas in a processing device, and a matter which is a chemical or a material mixing in.

Similarly, also in a liquid display element manufacturing process, if adherence of a particle to a pattern formed on a substrate of a liquid display element or any defects on the pattern occur, the substrate can not be used as a display element. Also, the same goes for a printed circuit board manufacturing process, and adherence of a particle may cause a short-circuit and insufficient connection on a pattern.

Conventionally, there is one technology, as disclosed in JP-A-62-89336, for detecting a particle on a semiconductor substrate of this type in which a laser beam is projected onto a semiconductor substrate to detect scattered light generated from a particle when the particle adheres to the semiconductor substrate and the detected light is compared with the inspection result obtained the adjacent inspection of a semiconductor substrate of the same product class, which eliminates disinformation from patterns and enables highly-sensitive and highly-reliable inspection of a particle and defect. Further, as disclosed in JP-A-63-135848, there is a technology in that a laser beam is projected onto a semiconductor substrate to detect scattered light generated from a particle when the particle adheres to the semiconductor substrate and the detected particle is analyzed by an analyzing technology such as laser photoluminescence or two dimension X-ray and Magnetic Resonance imaging (XMR) analysis.

Further, for a technology of inspecting such a particle as the above, a method is disclosed that a wafer is irradiated with coherent light and diffracted light produced from a repeating pattern on the wafer is removed by a spatial filter, thus the particle or defect without repeatability is highlighted to be detected. Further, a particle inspecting device is disclosed in JP-A-1-117024 in which a circuit pattern formed on a wafer is irradiated from the direction tilted at 45° to a group of main straight lines on the same pattern to prevent zero-order diffracted light from the group of main straight lines from entering the opening of an objective lens. In JP-A-1-117024, it is also described that the other group of straight lines other than the main straight lines are light-shielded by a spatial filter. Further, a conventional technology concerning a defect inspecting apparatus of a defect such as a particle etc. and a method thereof is disclosed in JP-A-2000-105203 in that a detection pixel size is changed by switching a detection optical system. A technology for measuring the size of a particle is disclosed in JP-A-2001-60607 and No. 2001-264264. JP-A-2004-177284 discloses a technology for detecting a defect on a thin film in that a laser beam is narrowed down to form a beam spot which is elongated in the direction perpendicular to a stage moving direction, and detection is performed in the direction perpendicular to an illumination direction.

BRIEF SUMMARY OF THE INVENTION

In the cases of JP-A-63-135848, No. 1-117024 and No. 2000-105203, the defect detection sensitivity fluctuates owing to changes in temperature or barometric pressure at a location where the defect inspecting apparatus is installed and sensitivity calibration frequency tends to increase due to the following reasons, improving deterioration in an operating rate of the apparatus due to frequent calibration is a challenge.

To detect a microscopic defect in the process of a recent, miniaturized semiconductor, in a defect inspecting apparatus, the SN of a defect signal strength is enhanced by reduction in a detection pixel size. The reduction in the detection pixel size makes the focal depth of a detection optical system shallow, therefore the relative refractive index of a detection lens is changed and a body tube is expanded thermally owing to fine changes in temperature or barometric pressure, thus the height of imaging of a defect is displaced, accordingly the image defocuses to decrease detection sensitivity. A clean room in which a defect inspecting apparatus is installed often provides an insufficient distance from adjacent equipment or a wall, and a local temperature in the environment of installation may change in about an hour. Keeping the detection sensitivity needs sensitivity calibration, but more frequent calibration may lower the operating rate of the apparatus because one calibration requires several minutes. For measures against it, there is a method of installing an apparatus in a dedicated thermal chamber, but because of disadvantages that the apparatus may be expensive and a footprint may be enlarged, this method is not suitable for a defect inspecting apparatus. Further, on the one hand, because barometric pressure in a clean room is not controlled, the sensitivity may become unstable when a low or high atmospheric pressure passes.

An object of the present invention is, to solve the above problems, to provide a defect inspecting apparatus configured so that a height of imaging can be corrected in real time for changes in temperature and barometric pressure.

To achieve the above object, in the invention, a mechanism in which a change in temperature or barometric pressure decreases the sensitivity was studied and measures against it were devised. More specifically, the mechanism is such that temperature and barometric pressure at a location of installation of the defect inspecting apparatus may have deviation from temperature and barometric pressure under which the sensitivity was adjusted up to a maximum in the same conditions and accordingly a height of imaging of a defect varies, and therefore measures are that a defect inspecting apparatus is provided which includes a construction for correcting the height of an object surface or image surface in real time for a change in at least either temperature or barometric pressure so that the image of an inspected substrate formed on an image sensor by a detection lens does not defocus. That is, a temperature of an inspection lens and a barometric pressure near the inspection lens are measured and a height of imaging for correction, or a height of the inspected substrate for correction when a sensor height is fixed, is derived from their deviation values, then after correction, inspection is carried out. The correction value is read out from a data table before inspection, which is created in advance from relation between temperature and barometric pressure, and the height of imaging, which is obtained in adjustment of the defect inspecting apparatus.

[Mechanism of Sensitivity Decrease Due to Change in Barometric Pressure]

A mechanism of the sensitivity decrease when barometric pressure falls is as follows. When barometric pressure falls, air density becomes small (proportionality relation), and therefore a relative refractive index of a detection lens becomes large and a focal length of the detection lens becomes small. As the result, a height of imaging becomes small, resulting in defocus and decrease in sensitivity. When barometric pressure rises, a mechanism is opposite to the falling case, the height of imaging becomes large, resulting in defocus and decrease in sensitivity. The height of an inspected substrate in relation to change in barometric pressure will be described with reference to FIG. 3. Plotted in the figure are heights of the inspected substrate at which the image of a defect does not defocus when an image sensor is fixed and barometric pressure in an apparatus changes. In the relation between the barometric pressure and the heights of the inspected substrate, the height of the inspected substrate changes linearly, because the relative refractive index between air and a lens is a linear function of barometric pressure. A shift $\Delta Z$ of a height of imaging when barometric pressure changes will be described with reference to FIG. 4. In imaging relation, an object surface is comprised of the inspected substrate 1, a lens is comprised of an upper detection optical system 200 and an imaging surface is comprised of an image sensor 205, and when barometric pressure rises, a focal length of the lens becomes large. Therefore, when a height of the image sensor is fixed, the height of the inspected substrate 1 may be lowered by $-\Delta Z$ to bring focus on the image sensor. On the contrary, when the inspected substrate 1 is fixed, it is necessary to raise the height of the image sensor by a longitudinal magnification of the detection lens, i.e. $\Delta Z \times$ the magnification$^2$.

[Mechanism of Sensitivity Decrease Due to Change in Temperature]

A mechanism of sensitivity decrease when temperature falls is as follows. When temperature falls, air density becomes large (proportionality relation), and therefore a relative refractive index of a lens becomes small and a focal length becomes large. As the result, a height of imaging becomes large, resulting in defocus and decrease in sensitivity. When temperature rises, a mechanism is opposite to the falling case, and the height of imaging becomes small to cause defocus of the image of a defect, resulting in sensitivity decrease. In addition, change in temperature has influence on elongation of a detection lens body tube, and the height of imaging varies complicatedly. For example, when temperature falls, a length of the lens body tube becomes small due to thermal expansion, and as the result, unless a position of the object surface is raised, the height of imaging defocuses to decrease the sensitivity.

[Data about Relation Between Temperature and Barometric Pressure, and a Height of an Object Surface or an Image Surface]

Using as a reference point standard environment which is regulated to, for example, 23° C. and 1,013 hPa and the height of an object surface or an image surface at which an image does not defocus under the environment, that is, the height of the object surface or the image surface having the maximal sensitivity under certain optical conditions, there is determined relation between barometric pressure and temperature measurements with respect to the reference point and a deviation of the height of the object surface or image surface at which imaging does not defocus when an environmental temperature at a location of installation of a defect inspecting apparatus is changed in a positive manner in adjustment, or when the environment changes. A data table for it will be described with reference to FIG. 5. Under the same optical conditions, i.e. the same detection magnification, the same illumination condition, the same substrate under test (a standard wafer for confirming sensitivity) and when a temperature at the location of installation of the defect inspecting apparatus is changed by ±2° C., a height of the inspected substrate Z at which the maximal sensitivity (maximal signal strength) may be obtained is found. The standard wafer for confirming sensitivity may be desirably, for example, a substrate formed by applying evenly particles of PSL uniform in size onto a silicon substrate. The height of the substrate Z is plotted by 1 μm a graph in which the ordinate axis represents barometric pressure and the abscissa axis represents temperature. In this example, the height of the substrate Z is in the unit of 1 μm, but a focal depth of a detection optical system may be desirably used as a minimal unit.

Because barometric pressure is proportional to gas density owing to a state equation, the height of the substrate approximately conforms to simulated data obtained from tracking a beam of light with barometric pressure being varied in an optical imaging simulator. Therefore, the simulated data as shown in FIG. 3 may be desirably used as data to create the data shown in FIG. 5.

[Correction Method]

Since temperature and barometric pressure are measured before inspection and a height of imaging or a position of an image sensor, i.e. a correction value for a height of an object surface or image surface corresponding to the temperature and barometric pressure is read from FIG. 5 to correct the height of the object surface or image surface to inspect, an operator can inspect not knowingly at a maximal sensitivity under selected optical conditions. Needless to say, without using the absolute data table in which the reference point is set as described above, it is also possible that a coefficient is derived in advance from relation between temperature and barometric pressure, and the height of the object surface or image surface, and then a correction value for the height of the object surface or image surface may be computed and obtained relatively by multiplying a deviation between two points of the temperature and barometric pressure with the coefficient.

More specifically, in a block diagram shown in FIG. 12, a control CPU portion 401 stores a Z coordinate (Z reference value) at which the maximal sensitivity is provided, a barometric pressure at that time (barometric pressure reference value), a temperature (temperature reference value) at that time, a coefficient obtained in advance for converting a barometric pressure into the Z coordinate (barometric pressure coefficient) and a coefficient for converting a temperature into the Z coordinate (temperature coefficient).

For correction of change in barometric pressure, a Z correction value is derived by adding a Z conversion value of barometric pressure for the change to a variation to the Z reference value, which Z conversion value is obtained by computing a difference between a measurement value by a barometric pressure measure 504 at an arbitrary time and the barometric pressure reference value and by multiplying it by the barometric pressure coefficient.

For correction of change in temperature, the Z correction value is derived by adding a Z conversion value of temperature for the change to a variation to the Z reference value, which Z conversion value is obtained by computing a difference between a measurement value by a temperature measure at an arbitrary time and the temperature reference value and by multiplying it by the temperature coefficient. Because the correction of change in barometric pressure and the correction of change in temperature function independently from each other, the Z correction value may be obtained by adding both of the Z conversion value based on barometric pressure and the Z conversion value based on temperature to the Z reference value, and by this correction value, concurrent correction of barometric pressure and temperature can be performed. A Z stage control unit 305 can locate a height of the inspected substrate at which the maximal sensitivity is provided, by changing a height of the Z stage 303 by the Z correction value.

As described above, the invention enables highly-sensitive detection of a defect wherein focal depth becomes shallow while stabilizing the sensitivity without lowering of the operating rate by calibration.

The invention is effective for change in the environment, and because the inspection lens and the environment change near the lens are measured, further countermeasures can be made against change in a temperature of an inspection lens caused by a local heat produced in the apparatus, such as a driving system of an inspection XY stage, a light source, sensors, controllers etc.

When the invention is applied, a thermostatic chamber is not required as measures for change in temperature, and therefore a size, cost and requirement for environment of equipment can be reduced.

The above features and other features than the above of the invention will be now described hereinafter. Other objects, features and advantages of the invention will become apparent from the following description of embodiments of the invention in conjunction with the accompanying drawings.

DESCRIPTION OF REFERENCE CHARACTERS

1—Inspected Substrate (Wafer),
2—Chip,
3—Slit-Like Beam (Illumination Region),
4—Detection Region of Image Sensor such as TDI Sensor,
100—Illumination Optical System
101—Laser Source,
102—Concave Lens,
103—Convex Lens,
104—ND Filter,
110—0-degree Illumination Beam Spot Imaging Portion
120—45-degree Illumination Beam Spot Imaging Portion (direction 10),
130—45-degree Illumination Beam Spot Imaging Portion (direction 11),
200—Vertical Detection Optical System,
201—Objective Lens (Detection Lens),
202—Spatial Filter,
203—Imaging Lens,
204—Zoom Lens Group,
205—One-Dimensional Detector such as TDI Sensor,
206—Sensor Z Driving System,
300—Stage System,
301-304—XYZθ Stage,
305—Stage Control,
400—A Control System,
401—Control CPU Portion,
402—Signal Processing Portion,
403—Display Portion,
404—Input Portion,
500—Oblique Detection System
501—Automatic Focus Unit,
502—Signal Processing Circuit,
503—Temperature Measure,
504—Barometric Pressure Measure.

DETAILED DESCRIPTION OF THE INVENTION

Embodiments of the invention will be described hereinafter with reference to the drawings. In the following drawings, similar functional portions are denoted by the same reference signs.

First, a substrate 1 to be inspected for a defect such as a particle etc. according to the invention will be described with reference to FIGS. 7 and 8. Since the details are described in Japanese Patent No. 3566589, the summary will be provided.

Figure 7:
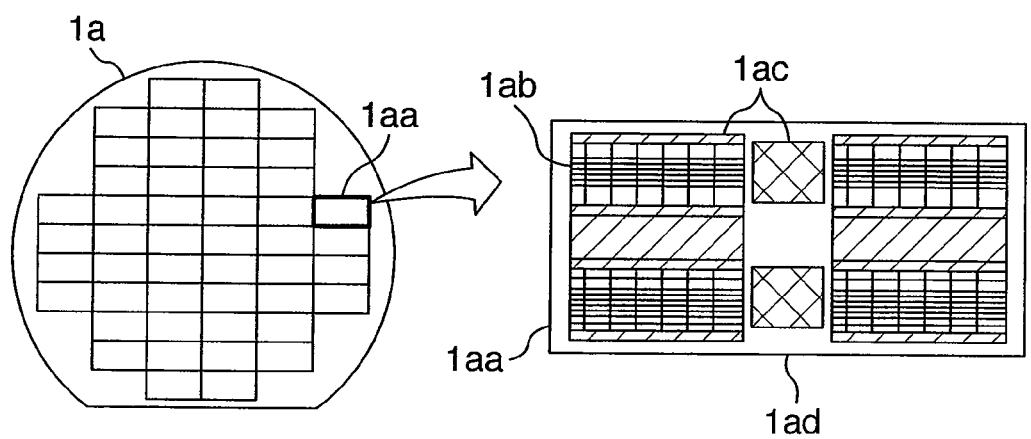
FIG. 7 is a view illustrating an inspected substrate on which memory LSIs, i.e. samples to be inspected, are arranged.

The substrate 1 to be inspected for a defect such as a particle etc. may be, as shown in FIG. 7, a semiconductor wafer 1a on which chips 1aa comprised of memory LSIs are arrayed two-dimensionally at predetermined intervals. The chip 1*aa* comprised of the memory LSI is mainly formed with a memory cell region 1*ab*, a peripheral circuit region 1*ac* comprised of a decoder, a control circuit and the like, and another region 1*ad*. The memory cell region 1*ab* is formed by arraying (repeatedly) a memory cell pattern two-dimensionally and regularly. However, the peripheral circuit region 1*ac* is formed by arraying a pattern two-dimensionally, but not regularly and repeatedly.

Figure 8:
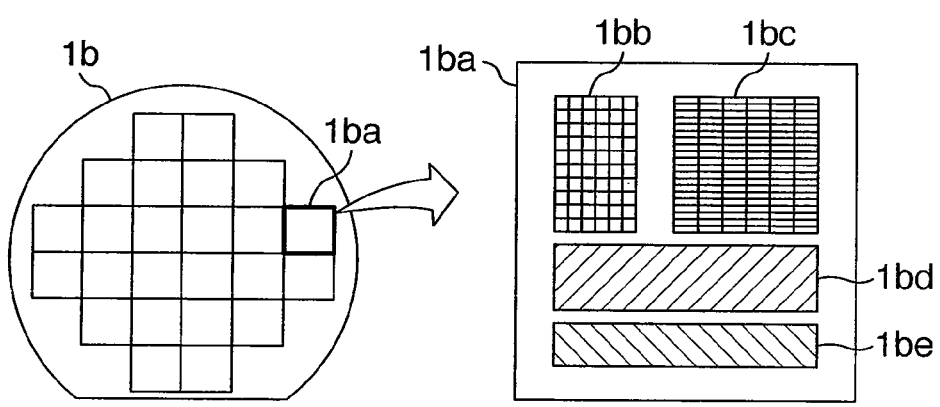
FIG. 8 is a view illustrating an inspected substrate on which LSIs such as microcomputers etc., i.e. samples to be inspected, are arranged.

The substrate 1 to be inspected for a defect such as a particle etc. may be, as shown in FIG. 8, a semiconductor wafer 1*b* on which chips 1*ba* comprised of LSIs such as microcomputers etc. are arrayed two-dimensionally at predetermined intervals. The chip 1*ba* comprised of the LSI such as a microcomputer etc. is mainly formed of a register group region 1*bb*, a memory region 1*bc*, a CPU core region 1*bd* and an input/output region 1*be*. Incidentally, FIG. 8 conceptually shows the array of the memory region 1*bc*, the CPU core region 1*bd* and the input/output region 1*be*. The register group region 1*bb* and the memory region 1*bc* are formed by arranging patterns two-dimensionally and regularly (repeatedly). The CPU core region 1*bd* and the input/output region 1*be* are formed by arranging nonrepeating patterns. As described above, as for the inspected substrate 1 to be inspected for a defect such as a particle etc., even when a semiconductor wafer is addressed, although the chips are arranged regularly, in the chip, a minimal line width is different in each region, and further it is considered that there may be various arrangements such as a repeating patter, nonrepeating pattern and the like.

The defect inspecting apparatus of a particle etc. and a method thereof according to the invention are based on an apparatus that in such an inspected substrate 1 as above, zero-order diffracted light produced from a pattern (linear pattern) comprised of a group of lines on a nonrepeating pattern region in the chip is blocked to enter an entrance pupil of an objective lens and scattered light produced by a defect such as a particle etc. present on the nonrepeating pattern region is received, thereby allowing a signal caused from the defect such as a particle etc. to be detected and a position coordinate of the defect to be computed. The details are described for instance in Japanese Patent No. 3566589 (particularly, see paragraphs 0033 to 0036), and here the explanation will be omitted.

Next, a first embodiment of the defect inspecting apparatus according to the invention will be described with reference to FIG. 1.

The first embodiment of the defect inspecting apparatus includes: a stage portion 300 composed of an X stage 301, Y stage 302, Z stage 303 capable of focusing on a surface of an inspected substrate, theta (θ) stage 304 and stage controller 305; a laser source 101; a concave lens 102; and a convex lens 103. The apparatus further includes: an illumination optical system 100 comprising a beam expander, a beam formation portion composed of an optical filter group 104 and a mirror 105, and three sets of a beam spot imaging portion composed of a transparent glass plate and a switchable optical branching element (or a mirror) 106, an illumination lens with a cylindrical curved surface 107 and mirrors 108, 109; a detection optical system comprising a detection lens 201, a spatial filter 202, an imaging lens 203, a zoom lens group 204 and a one-dimensional sensor (image sensor) 205 such as TDI etc.; an optical system 500 comprising a lens and a sensor for detection at a low elevation angle; a control system 400 comprising a signal processing system 402 composed of an A/D conversion portion, a data memory which may be delayed, a difference processing circuit for obtaining a difference between signals of chips, a memory for storing temporarily a difference signal between the signals of the chips, a threshold computation processing portion for setting a pattern threshold and a comparison circuit, an output means for storing a detection result of a defect such as a particle etc. and outputting the detection result of a defect, a computation processing system 401 for controlling driving of a motor etc., a coordinate and an image sensor, a display system 403, and an input system 404. The defect inspecting apparatus is on the system that a defect on the inspected substrate is illuminated at a slant, the inspected substrate which is mounted on the XY stage is scanned in a predetermined direction and light generated by the defect is received by the detection optical system disposed on the upper side, and the apparatus is characterized by including a mechanism which corrects a height of imaging in real time for change in temperature and barometric pressure so that an image does not defocus. The detection optical system 200 disposed on the upper side described above can detect a more microscopic defect and a defect equal to or smaller than a limit value of resolving power, by including a magnifying lens to receive scattered light from the defect with a high NA, and magnifying and projecting it with a high magnification on the image sensor to inspect in a small pixel size.

Figure 2:
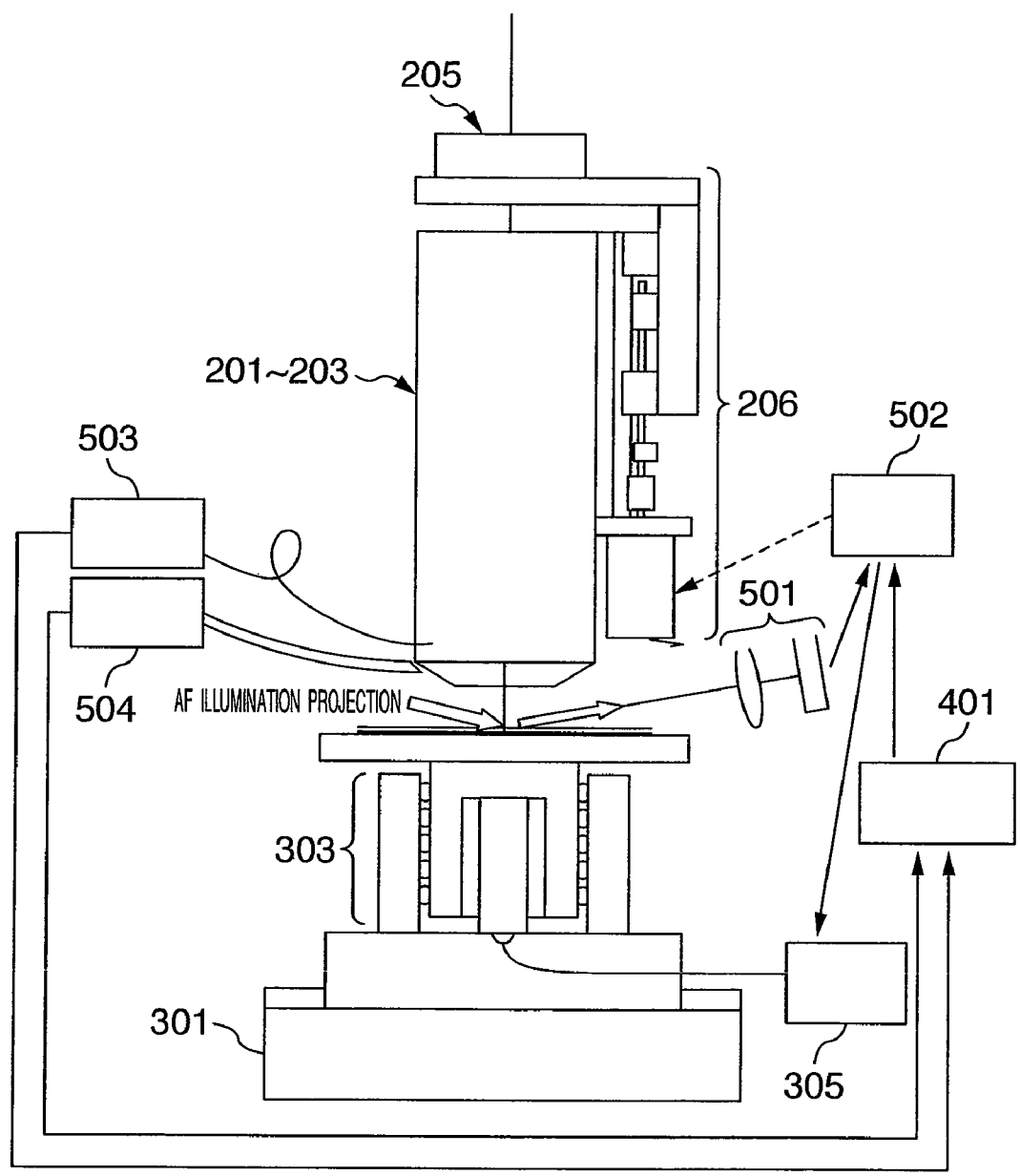
FIG. 2 is a view illustrating the configuration of a system according to the invention.
Figure 3:
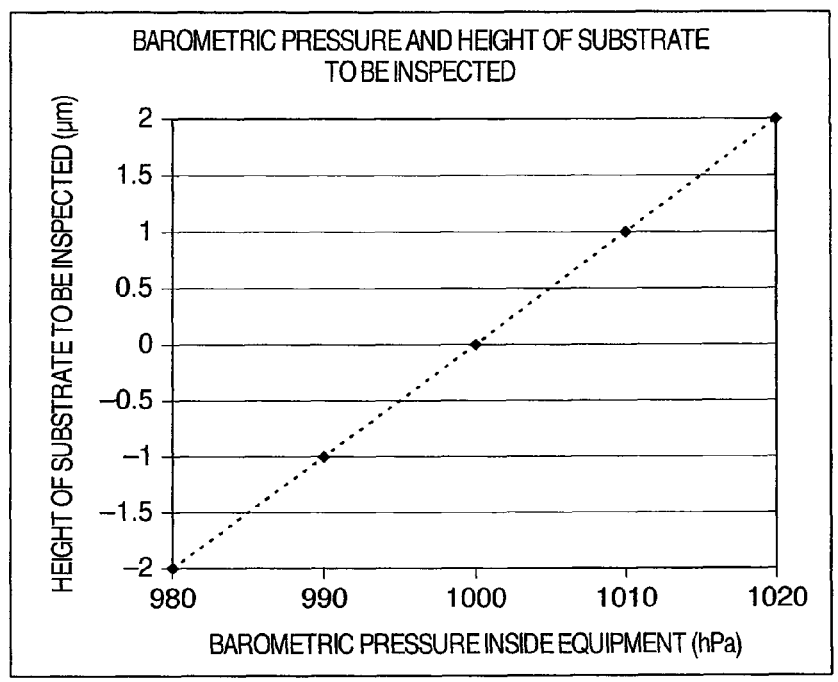
FIG. 3 is a graph showing relation between barometric pressure and the height of an inspected substrate in focus.
Figure 4:
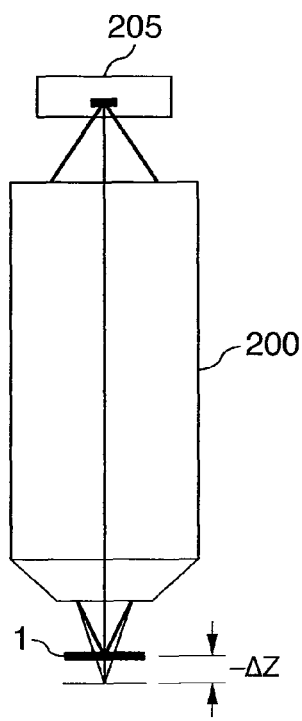
FIG. 4 is a view explaining that the height of an inspected substrate is varied by change in barometric pressure.
Figure 5:
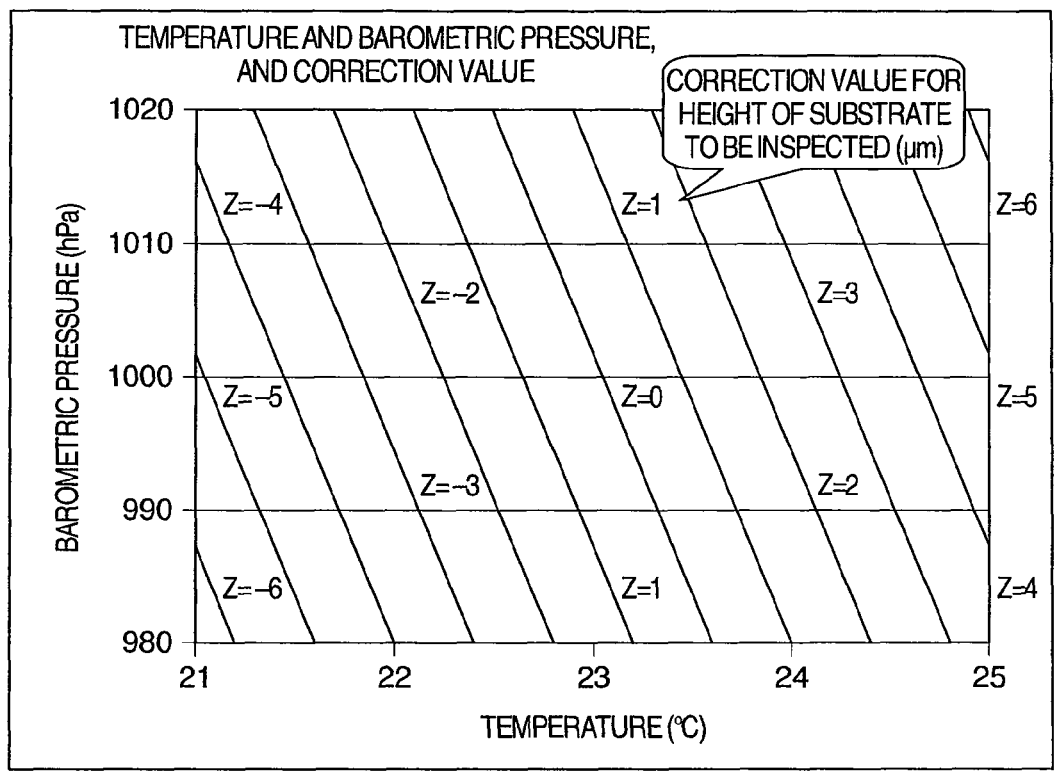
FIG. 5 is a graph of relation between temperature and barometric pressure and a correction amount for the height of an inspected substrate.

A unit according to the invention will be described using FIG. 2. The unit includes: an automatic focus system 501 having a position sensor and an imaging light path of off-axis for projecting and receiving a light beam which dose not pass through a lens in the detection lens 201; a signal processing circuit 502; the X stage 301, the Z stage 303 as a stage Z mechanism for controlling the height of the inspected substrate to correct the height of an object surface; the stage control system 305; the image sensor 205; the image sensor Z-direction driving system 206 as a Z mechanism for moving up and down the image sensor to correct the height of imaging; the control CPU portion 401; a barometric pressure measure 504; and a temperature measure 503. The control CPU portion 401, the stage control system 305 and the signal processing circuit 502 form a control system for converting a deviation of at least either temperature or barometric pressure into a correction value for the position of an object surface or image surface and for locating the object surface or image surface, and can drive the image sensor Z-direction driving system 206 or the Z stage 303 to correct the height of the object surface or image surface in real time for change in at least either temperature or barometric pressure so that an image of the inspected substrate formed on the image sensor by the detection lens does not defocus. As for measurement of temperature and barometric pressure, in order to reduce an error due to a gradient of temperature and barometric pressure, it is desirable to attach a sensor portion so that the inside or the surface of the detection lens 201 can be measured. A result measured by the barometric pressure measure 504 and the temperature measure 503 is sent to the control CPU portion 401, a correction value ΔZ is read out based on a data table prepared from the graph of FIG. 5 described above, and then a command as an offset value is sent to the signal processing circuit 502. The signal processing circuit 502 drives the stage Z in a closed loop until the offset value corresponding to the correction value ΔZ is provided by the automatic focus system 501. When the height of the inspected substrate is corrected, a spot 3 of a separate illumination system is displaced separately, and therefore it becomes necessary to have a function for correcting automatically the position of the spot 3 to the center.

In this embodiment, also by using the image sensor Z-direction driving system 206 and by relatively moving a value of ΔZ×magnification², a height of the image sensor 205 may be varied so that the image sensor can be located at a height of imaging displaced due to temperature or barometric pressure and imaging with no defocus can be obtained. Autofocusing illumination light is configured in a manner that it has an illumination path in a space which does not interfere with the detection lens, and illuminates the inspected substrate to provide dark-field illumination, and reflected light provides an image on an opposite position sensor. The autofocusing system uses desirably a light source having a wideband wavelength for preventing the light from interfering with a pattern of a particular film thickness on the inspected substrate to lower signal strength. On the one hand, the detection lens is designed to bring out an imaging performance to a diffraction limit at a single, inspection illumination wavelength, and therefore when the autofocusing light path is designed to be shared with the detection lens, the lens becomes expensive largely. Particularly, when a detection illumination wavelength is short and has a large difference from an autofocusing illumination wavelength, it is difficult to design the lens and an off-axis specification may be desirably applied.

Figure 6:
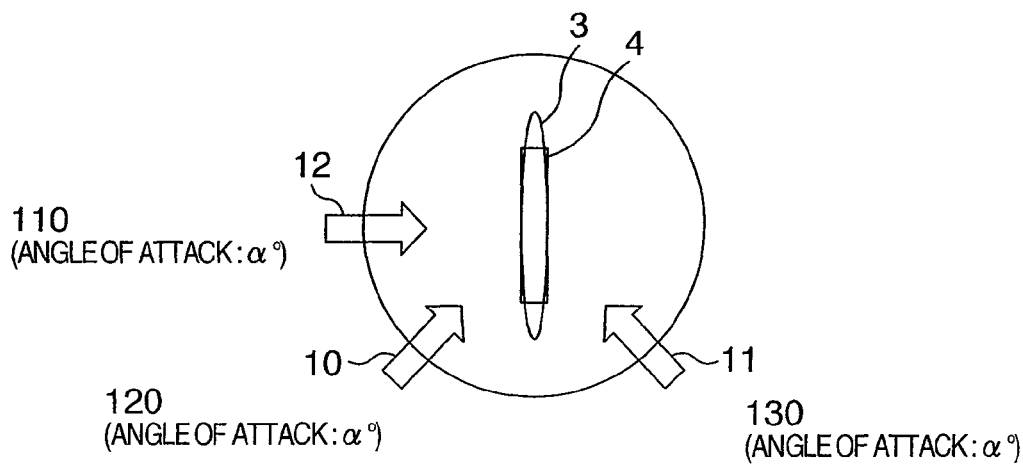
FIG. 6 is a view for explanation of a spot formed by illuminating a projection plane of an image sensor on an inspected substrate from three directions.

The three illumination optical systems 100 are configured in a manner that a light beam emitted from the laser source 101 passes through the beam expander composed of the concave lens 102 and the convex lens 103, and through the illumination lens 107 having a cylindrical curved surface so that a slit-like beam 3 irradiates the substrate (wafer) 1 to be inspected from three directions 10, 11 and 12 in a plane as shown in FIG. 6 with the longitudinal direction of the slit-like beam 3 facing the array direction of the chips. The array direction of the chips corresponds to a detection region 4 of the sensor. Incidentally, the reason why the slit-like beam 3 is used as the illumination light is that a scan width large in the X direction is made large and inspection of a defect such as a particle etc. is sped up. Further, the slit-like beam 3 from the three directions 10, 11, 12 may irradiate the substrate selectively from one direction or two directions 10, 12 concurrently by switching a beam splitter or the mirror 106 to a transparent glass plate of the same thickness. The longitudinal direction of the slit-like beam 3 is turned toward the array direction of the chips with respect to the inspected substrate 1 and perpendicular to a scan direction Y of the Y stage 302. This allows simplifying comparison of a pixel signal between the chips and facilitating computation of a position coordinate of a defect, thereby speeding up inspection of a defect such as a particle etc.

Figure 9:
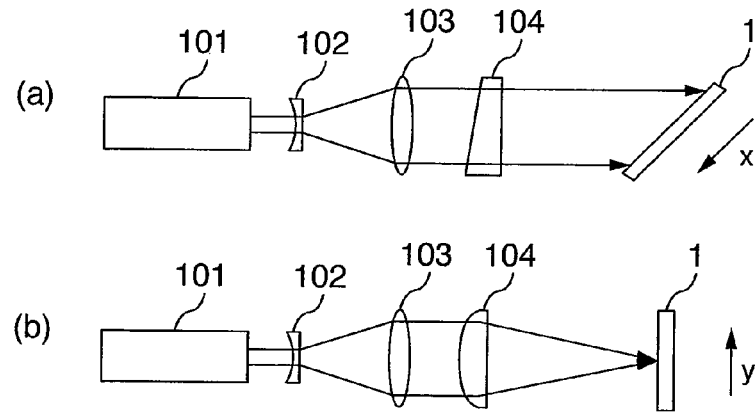
FIG. 9 is a view illustrating an optical system, including an illumination lens of an illumination optical system, of the defect inspecting apparatus according to the invention.
Figure 10:
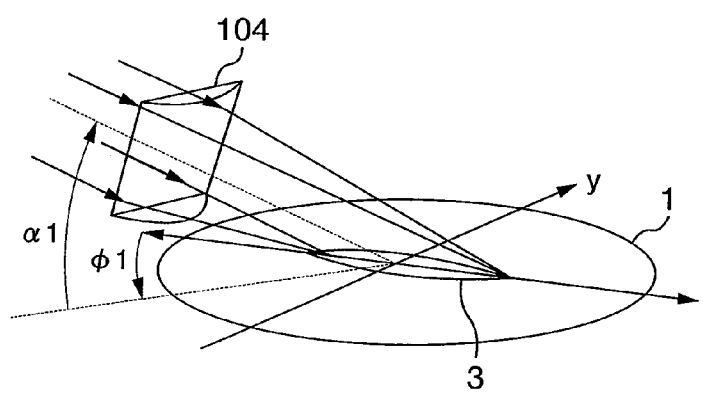
FIG. 10 is a view illustrating the function of the illumination lens of the illumination optical system in the defect inspecting apparatus according to the invention.

FIGS. 9, 10 show an illumination lens 104 having a circular cone shape and a cylindrical curved surface. A manufacturing method etc. of the illumination lens 104 having the cylindrical curved surface is described in detail, for example, in Japanese Patent No. 3566589 (particularly, see paragraphs 0027 and 0028) and it may be manufactured by the known method. The illumination lens 104 of a circular cone shape is a lens having different focal lengths at positions in the longitudinal direction of a cylindrical lens, which lengths are varied linearly. With this configuration, even when illumination is provided at a slant (having tilts φ1, α1) as shown in FIG. 10, the slit-like beam 3 narrowed down in the Y direction and collimated in the X direction can irradiate. That is, according to this illumination lens 104, illumination having a collimated light beam in the X direction can be provided at near φ1=45°, as shown in FIG. 9(a). Especially, as shown in FIG. 9(a), the slit-like beam 3 is collimated in the X direction, and accordingly a diffracted light pattern can be obtained from a circuit pattern having a main group of lines facing the X or Y direction and be light-shielded by the spatial filter 202.

The illumination lens 104 having the cylindrical curved surface can form the slit-like beam 3 shown in FIG. 10.

Figure 1:
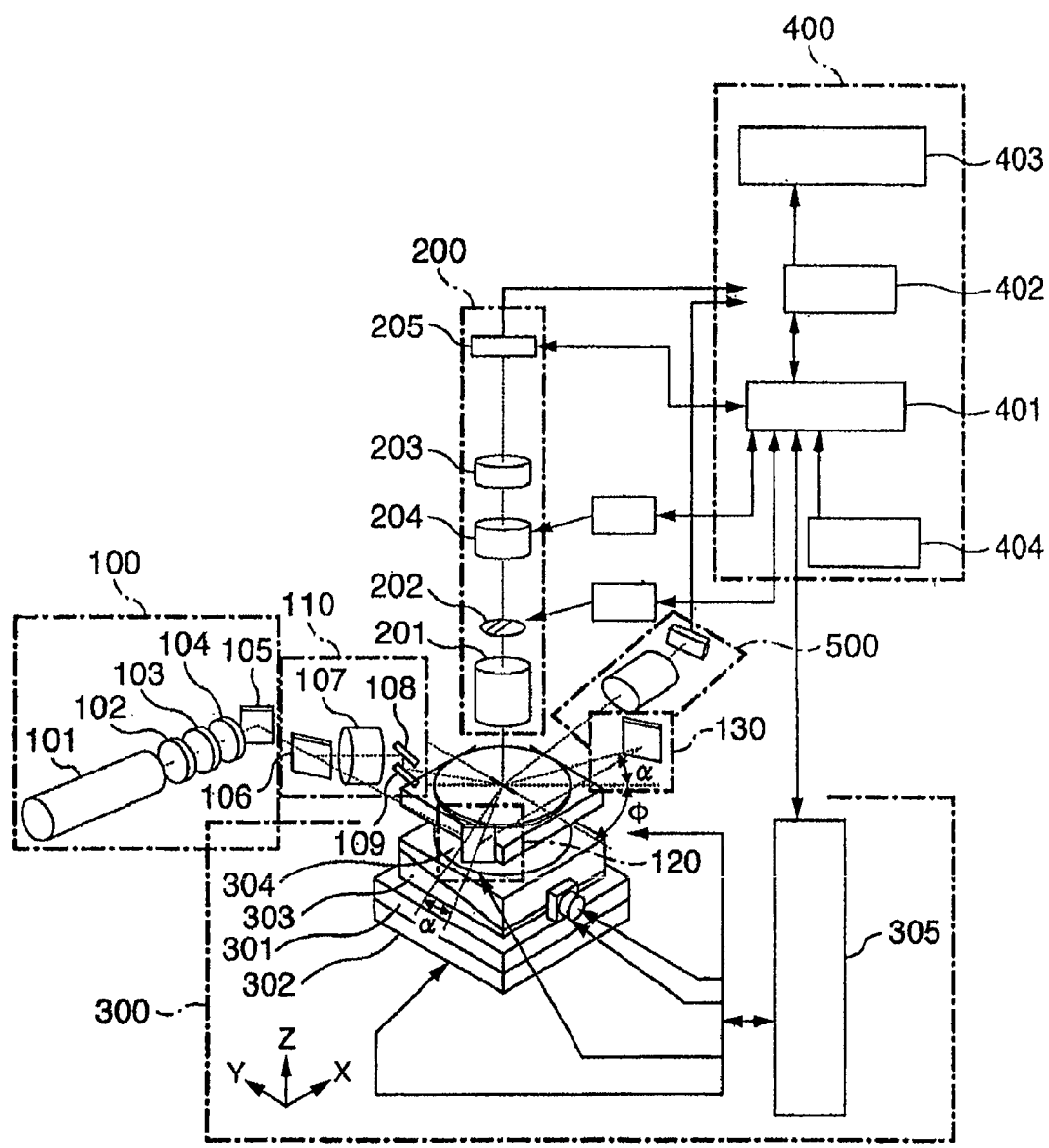
FIG. 1 is view illustrating system configuration of a defect inspecting apparatus.
Figure 11:
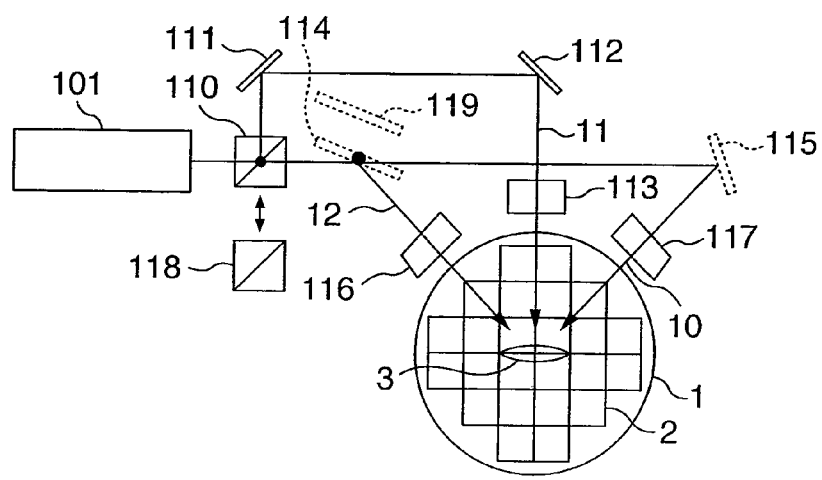
FIG. 11 is a view for explanation of an illumination optical system.
Figure 12:
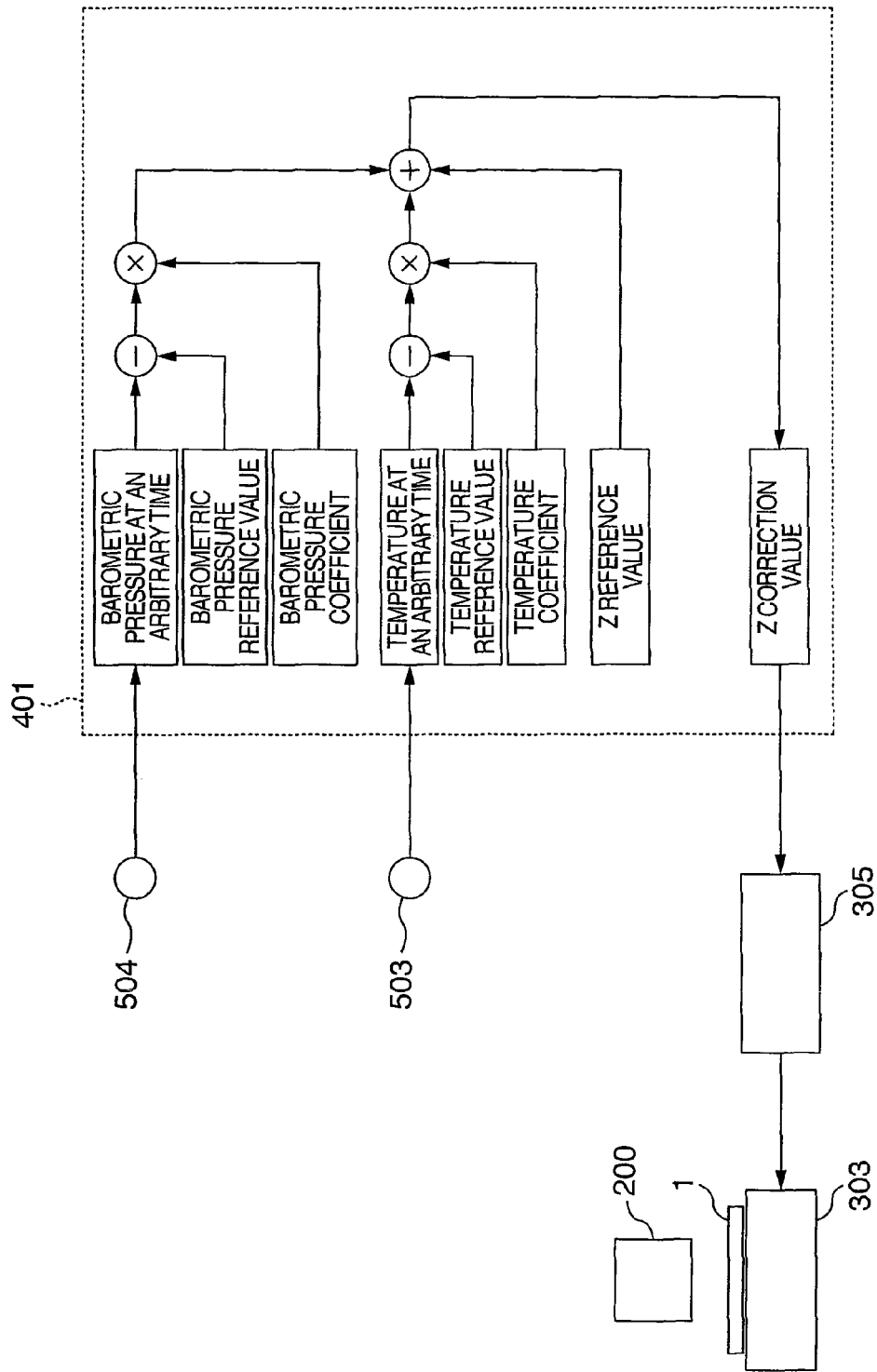
FIG. 12 is a schematic view illustrating the principle of the invention that the height of a Z stage is corrected by using a coefficient of a conversion formula.

FIG. 11 is a plan view illustrating the illumination optical system 100 having the three beam spot imaging portions in FIG. 1. A laser beam emitted from the laser source 101 is branched into two light paths by a branching optical element 110 such as a half mirror etc., and one of the branched beams is reflected by mirrors 111, 112 and turned downward by a mirror 113 to enter the concave lens 102, thereby providing an illumination beam from the direction 11, and the other beam progresses to a branching optical element 114 such as a half mirror etc. One branched by the branching optical element 114 is reflected by a mirror 115 and turned downward by a mirror 117 to enter the concave lens 102, thereby providing an illumination beam from the direction 10, and the other is turned downward by a mirror 116 to enter the concave lens 102, providing an illumination beam from the direction 10. By the way, illumination only from the direction 11 can be provided by switching the branching optical element 110 to a mirror element 118. Also, illumination only from the directions 10 and 12 can be provided by removing the branching optical element 110 from the light path or by switching it to a transparent optical element. Further, illumination only from for example, the direction 12 selected from the two directions 10 and 12 can be provided by switching the branching optical element 114 to a mirror element 119.

Besides, for the laser source 101, the third higher harmonic wave THG of a high-power YAG laser with a wavelength of 355 nm may be used because of branching, but it is not necessarily limited to 355 nm. Also, the laser source 101 is not necessarily of YAG THG. That is, the laser source 101 may be another laser source such as an Ar laser, nitrogen laser, He—Cd laser, excimer laser and the like.

The detection optical system 200 is configured in a manner that light outgoing from the wafer 1 is detected by using the detection lens (objective lens) 201, the spatial filter 202 for light-shielding a Fourier transform image out of reflected, diffracted light from a repeating pattern, the imaging lens 203, and the one-dimensional sensor 205 such as TDI etc. The spatial filter 202 is disposed at a height of imaging in a spatial frequency region of the objective lens 201, i.e. a Fourier transform (corresponding to a projecting pupil) in order to light-shield the Fourier transform image out of the reflected, diffracted light from the repeating pattern. Here, an image of an illumination area 3 on the wafer 1 shown in FIG. 7 is formed on the image sensor 205 by the object lens 201 and imaging lens 203 constituting a relay lens. A light-receiving area of the one-dimensional sensor 205 such as TDI etc. is denoted by 4.

When the inspected substrate 1 having the circuit patterns of various forms formed thereon as described above is irradiated with the slit-like beam 3, the reflected, diffracted light (or scattered light) is projected from the surface of the wafer, the circuit patterns, and a defect such as a particle. This projected light is received by the image sensor 205 through the detection lens 201, spatial filter 202 and imaging lens 203 and is converted photoelectrically. In illuminance (power) of light beam flux emitted from the illumination optical system such as the laser source 101 etc., its dynamic range may be changed by controlling a ND filter 104 or laser power to change.

Further, the inspected substrate (wafer) 1 has to be inspected for a particle or a defect, the residue after etching and the like intruding in a concave portion between wires etc. However, because the nonrepeating pattern is present on the inspected substrate 1, in order to prevent zero-order diffracted light from the nonrepeating pattern from entering the objective lens 201, as described above, the substrate 1 is irradiated with the slit-like beam 3 arranging its longitudinal direction in the X direction from the directions 10, 12 which forms an angle of about 45° to the Y axis. This makes it difficult to irradiate the concave portion sufficiently, because the wires etc. form convex portions and block the slit-like beam 3.

Then, since a wiring pattern is often formed in the perpendicular and parallel direction, the substrate 1 may be irradiated with the slit-like beam 3 from the direction 11 parallel to the Y axis, which allows the concave portion between wires etc. to be sufficiently irradiated. Particularly, a wiring pattern of a memory LSI is often a linear pattern having a length of several mm, therefore illumination from this direction 11 may allow often inspection. Also, depending on a pattern, when in the direction of 90°, rotating the wafer by 90°, or setting the illumination direction to the X direction allows inspection.

Next, the spatial filter 202 will be described. The chip 2 includes a repeating pattern such as the memory cell region 1ab in the memory LSI 1aa, the register group region 1bb in the LSI 1ba such as a microcomputer etc., and the memory region 1bc, and it is required to light-shield a diffracted light pattern (diffraction interference pattern) generated from this repeating pattern by the spatial filter 202. In a word, a repeating pattern, nonrepeating pattern and absence of a pattern are mixed on the chip 2 and moreover a line width is different from each other. Therefore a light-shielding pattern of the spatial filter 202 is usually set so that diffracted light from, for example, a repeating pattern which frequently appears is eliminated. Further, when a spatial filter 202 with a variable light-shielding pattern as described in JP-A-5-218163 and No. 6-258239 is used, it may be changed depending on a circuit pattern in the chip 2. Alternately, spatial filters of different light-shielding patterns may be provided as the spatial filter 202, and they may be switched depending on a circuit pattern in the chip 2. However, when the slit-like beam 3 is emitted from the direction 11, it becomes necessary to light-shield zero order diffracted light by the spatial filter 202 to eliminate it. At this time, it is also obviously possible to light-shield high-order diffracted light to eliminate it by the spatial filter 202. As above, the eliminating method of diffracted light has been described in the case of the repeating or nonrepeating pattern present in the chip 2 on the inspected substrate 1.

Next, description will be made on detection sensitivity adjustment corresponding to the size of a defect such as a particle to be detected. When a detection pixel size of the one-dimensional sensor (image sensor) 205 such as TDI etc. above the inspected substrate 1 is made small, although the throughput drops, improvement of the detection sensitivity may be expected. Consequently, when a defect such as a particle smaller than about 0.1 μm is to be detected, the detection optical system 200 may be changed to a system in which a pixel size is made smaller. More specifically, three kinds of detection optical system 200 may be provided, in which concerning the pixel size of the image sensor etc., an image size on the wafer 1 is made variable. A realization method of this configuration is that the lens groups 204 are switched. At this time, a configuration of the lenses may be designed so that a light path length from the wafer 1 to the one-dimensional sensor 205 such as TDI etc. needs not to be changed. Also, when such a design is difficult, in addition to switching the lenses, a mechanism for changing a distance to the image sensor may be used. Further, image sensors having different pixel sizes in themselves may be switched.

It will be apparent to those skilled in the art that although the forgoing description has been made on the embodiments of the invention, the invention is not limited thereto, and various changes and modifications may be made within the sprit of the invention and the scope of the appended claims.

The invention claimed is:

1. A method for detecting a defect of a substrate, the method comprising steps of:
    irradiating the substrate with a first light;
    detecting a second light from the substrate and forming an image of an illuminated area on the substrate;
    measuring an environment of a defect inspecting apparatus, wherein said environment includes a temperature and barometric pressure; and
    while inspecting the substrate, changing at least one of a height of a surface of the substrate and a height of a surface of the image based on a table,
    wherein said table is used for converting at least one of a deviation from a standard height of a standard substrate surface relative to a change of said environment, and a deviation from a standard height of an image surface relative to change of said environment.

2. The method according to claim 1, the changing step comprising:
    correcting a position of an image sensor involved in forming the image.

3. The method according to claim 1, the changing step comprising:
    changing a height of the substrate.

4. A defect inspecting apparatus comprising:
    an illuminating unit which irradiates a substrate with a first light;
    a detection unit which detects a second light from the substrate and forms an image of an illuminated area on the substrate;
    a plurality of measurement units which measure an environment of the defect inspecting apparatus, wherein said environment includes a temperature and barometric pressure; and
    a correcting unit which changes at least one of a height of a surface of the substrate and a height of a surface of the image, wherein:
        said correcting unit uses a deviation of said environment, and a plurality of coefficients, and
        said coefficients are acquired by at least one of a relationship between said environment and a height of said surface of the substrate, and a relationship between said environment and said image surface.

5. A method for detecting a defect of a substrate, the method comprising steps of:
    illuminating the substrate with a first light;
    detecting a second light from the substrate;
    forming an image of an illuminated area on the substrate;
    measuring an environment, wherein said environment includes a temperature and barometric pressure; and
    changing at least one of a height of a surface of the substrate and a height of a surface of the image, wherein:
        during said changing step, a deviation of said environment and a plurality of coefficients are used, and
        said coefficients are acquired by at least one of a relationship between said environment and a height of said surface of the substrate, and a relationship between said environment and said image surface.

* * * * *